(12) United States Patent
Thesman

(10) Patent No.: US 11,562,814 B2
(45) Date of Patent: *Jan. 24, 2023

(54) HIERARCHICAL CONDITION CATEGORIES PROGRAM

(71) Applicant: HCC Investments, LLC, Rocklin, CA (US)

(72) Inventor: Debra Thesman, Marina Del Rey, CA (US)

(73) Assignee: HCC INVESTMENTS, LLC, Carson City, NV (US)

( * ) Notice: Subject to any disclaimer, the term of this patent is extended or adjusted under 35 U.S.C. 154(b) by 401 days.

This patent is subject to a terminal disclaimer.

(21) Appl. No.: 16/869,328

(22) Filed: May 7, 2020

(65) Prior Publication Data

US 2020/0265935 A1 Aug. 20, 2020

Related U.S. Application Data

(63) Continuation of application No. 15/691,413, filed on Aug. 30, 2017, now Pat. No. 10,699,805, which is a
(Continued)

(51) Int. Cl.
*G16H 10/60* (2018.01)
*G06Q 10/10* (2012.01)
(Continued)

(52) U.S. Cl.
CPC ........... *G16H 10/60* (2018.01); *G06Q 10/101* (2013.01); *G09B 19/00* (2013.01); *G16H 15/00* (2018.01); *G16H 70/20* (2018.01)

(58) Field of Classification Search
CPC ........ G16H 10/60; G16H 15/00; G16H 70/20; G06Q 10/101; G09B 19/00
See application file for complete search history.

(56) References Cited

U.S. PATENT DOCUMENTS

| 6,014,629 A | 1/2000 | DeBruin-Ashton |
| 6,067,524 A | 5/2000 | Byerly |

(Continued)

FOREIGN PATENT DOCUMENTS

WO WO-2007149675 A2 * 12/2007 ............ A61B 5/00

OTHER PUBLICATIONS

Stuart, Medication Patterns for Medicare Beneficiaries with SNF/LTC Facility Stays, Spring 2008, Health Care Financing Review, vol. 29, No. 3, pp. 13-25. (Year: 2008).*

(Continued)

*Primary Examiner* — Christopher L Gilligan
(74) *Attorney, Agent, or Firm* — Stetina Brunda Garred & Brucker

(57) ABSTRACT

Systems and methods of recording patient's medical documents and training programs for improving medical document recordation. The system includes a computer readable medium capable of storing medical data obtained from patients, including disease codes, a computer with software capable of evaluating the data stored on the computer readable medium for completeness, and a notification system capable of presenting to the user of the system a warning if any of the data is found to be incomplete or incorrect. The training includes evaluating the healthcare provider's current medical documentation process, training the healthcare provider in methods of recording medical documents, providing a system for recording medical documents, and training the healthcare provider in use of the system.

4 Claims, 1 Drawing Sheet

Related U.S. Application Data continuation of application No. 14/326,754, filed on Jul. 9, 2014, now abandoned, which is a continuation of application No. 13/167,976, filed on Jun. 24, 2011, now abandoned.

(51) Int. Cl.
*G16H 15/00* (2018.01)
*G16H 70/20* (2018.01)
*G09B 19/00* (2006.01)

(56) References Cited

U.S. PATENT DOCUMENTS

| | | | |
|---|---|---|---|
| 6,240,394 B1 | 5/2001 | Uecker | |
| 6,263,330 B1 | 7/2001 | Bessett | |
| 6,283,761 B1 | 9/2001 | Joao | |
| 6,298,348 B1 | 10/2001 | Eldering | |
| 6,341,265 B1 | 1/2002 | Provost | |
| 6,343,271 B1 | 1/2002 | Peterson et al. | |
| 6,735,569 B1 | 5/2004 | Wizig | |
| 6,802,810 B2 | 10/2004 | Ciarniello et al. | |
| 6,820,058 B2 | 11/2004 | Wood et al. | |
| 6,824,052 B2 | 11/2004 | Walsh | |
| 7,016,856 B1 | 4/2006 | Wiggins | |
| 7,039,458 B2 | 5/2006 | Ueda et al. | |
| 7,251,610 B2 | 7/2007 | Alban et al. | |
| 7,275,220 B2 | 9/2007 | Brummel et al. | |
| 7,464,041 B2 | 12/2008 | Merkin | |
| 7,483,838 B1 | 1/2009 | Marks | |
| 7,490,048 B2 | 2/2009 | Joao | |
| 7,533,353 B2 | 5/2009 | Dvorak et al. | |
| 7,657,442 B2 | 2/2010 | Merkin | |
| 7,698,154 B2 | 4/2010 | Marchosky | |
| 7,702,524 B1 | 4/2010 | Whibbs et al. | |
| 7,734,656 B2 | 6/2010 | Bessette et al. | |
| 7,742,930 B1 | 6/2010 | Calhoun, Jr. et al. | |
| 7,801,744 B2 | 9/2010 | Patterson | |
| 7,856,456 B2 | 12/2010 | Bessette | |
| 7,881,950 B2 | 2/2011 | Petterson | |
| 7,899,689 B1 | 3/2011 | Wizig | |
| 7,904,313 B2 | 3/2011 | Knight | |
| 7,917,438 B2 | 3/2011 | Kennedy et al. | |
| 7,958,002 B2 | 6/2011 | Bost | |
| 7,984,079 B2 | 7/2011 | Bessette | |
| 8,050,945 B2 | 11/2011 | Patterson | |
| 8,060,376 B2 | 11/2011 | Horner | |
| 8,262,394 B2 | 9/2012 | Walker et al. | |
| 8,285,565 B2 | 10/2012 | Kerr et al. | |
| 8,289,750 B2 | 10/2012 | Krishnan et al. | |
| 8,290,789 B2 | 10/2012 | Wennberg | |
| 8,296,333 B2 | 10/2012 | Bessette | |
| 8,308,062 B1 | 11/2012 | Walton, III | |
| 8,311,855 B2 | 11/2012 | Kerr et al. | |
| 8,321,239 B2 | 11/2012 | Hansen et al. | |
| 8,326,648 B2 | 12/2012 | Kennedy et al. | |
| 8,332,466 B1 | 12/2012 | Cha et al. | |
| 8,335,696 B2 | 12/2012 | Brown | |
| 8,380,631 B2 | 2/2013 | Dala et al. | |
| 8,442,840 B2 | 5/2013 | Menocal et al. | |
| 8,452,617 B2 | 5/2013 | Kerr et al. | |
| 2001/0037214 A1 | 11/2001 | Raskin et al. | |
| 2002/0000247 A1 | 1/2002 | Michelson et al. | |
| 2002/0007290 A1 | 1/2002 | Gottlieb | |
| 2002/0019754 A1 | 2/2002 | Peterson et al. | |
| 2002/0026105 A1 | 2/2002 | Drazen | |
| 2002/0035316 A1 | 3/2002 | Drazen | |
| 2002/0120471 A1 | 4/2002 | Drazen | |
| 2002/0062226 A1 | 5/2002 | Ito | |
| 2002/0072933 A1 | 6/2002 | Vonk et al. | |
| 2002/0123906 A1 | 9/2002 | Goetzke et al. | |
| 2002/0149616 A1 | 10/2002 | Gross et al. | |
| 2003/0023598 A1 | 1/2003 | Janakiraman et al. | |
| 2003/0074228 A1 | 4/2003 | Walsh | |
| 2003/0078811 A1 | 4/2003 | Cole et al. | |
| 2003/0078813 A1 | 4/2003 | Haskell et al. | |
| 2003/0078911 A1 | 4/2003 | Haskell et al. | |
| 2003/0167183 A1 | 9/2003 | Kido et al. | |
| 2003/0167189 A1 | 9/2003 | Lutgen et al. | |
| 2003/0193448 A1 | 10/2003 | Tsui | |
| 2003/0212579 A1 | 11/2003 | Brown et al. | |
| 2004/0039600 A1* | 2/2004 | Kramer | G06Q 10/10 705/2 |
| 2004/0103022 A1 | 5/2004 | Chilcoat, III et al. | |
| 2004/0186744 A1 | 9/2004 | Lux | |
| 2005/0091077 A1 | 4/2005 | Reynolds | |
| 2005/0202383 A1 | 9/2005 | Thomas et al. | |
| 2006/0080146 A1 | 4/2006 | Cook et al. | |
| 2006/0085222 A1 | 4/2006 | Huang et al. | |
| 2006/0173711 A1* | 8/2006 | Rapier, III | G16H 40/20 600/300 |
| 2007/0122783 A1 | 5/2007 | Habashi | |
| 2007/0203760 A1 | 8/2007 | Schmidt et al. | |
| 2007/0244714 A1 | 10/2007 | McCluskey et al. | |
| 2008/0059224 A1 | 3/2008 | Schechter | |
| 2008/0086327 A1 | 4/2008 | Cox et al. | |
| 2009/0024417 A1 | 1/2009 | Marks et al. | |
| 2009/0113008 A1 | 4/2009 | Gonzalez et al. | |
| 2009/0254375 A1 | 10/2009 | Martinez et al. | |
| 2010/0114598 A1* | 5/2010 | Oez | G16H 15/00 705/2 |
| 2010/0131298 A1 | 5/2010 | Buttner et al. | |
| 2010/0028085 A1 | 11/2010 | Merkin | |
| 2011/0125531 A1* | 5/2011 | Seare | G06Q 10/00 705/2 |
| 2011/0145018 A1 | 6/2011 | Fotsch et al. | |
| 2011/0153348 A1 | 6/2011 | Kerr et al. | |
| 2011/0270632 A1 | 11/2011 | Manning et al. | |
| 2012/0191472 A1 | 7/2012 | Thesman | |
| 2012/0191487 A1 | 7/2012 | Merkin | |
| 2012/0226507 A1 | 9/2012 | Wendt | |
| 2012/0278094 A1 | 11/2012 | Kovacevic et al. | |
| 2012/0284044 A1 | 11/2012 | Bregante et al. | |
| 2012/0284055 A1 | 11/2012 | Hansan et al. | |
| 2012/0284056 A1 | 11/2012 | Hofstetter | |
| 2012/0284057 A1 | 11/2012 | Hansan et al. | |
| 2012/0290322 A1 | 11/2012 | Bergman et al. | |
| 2012/0296665 A1 | 11/2012 | Merkin | |
| 2012/0303378 A1 | 11/2012 | Lieberman | |
| 2012/0303381 A1 | 11/2012 | Bessette | |
| 2012/0329015 A1 | 12/2012 | Thesman | |
| 2013/0030838 A1 | 1/2013 | Myers et al. | |
| 2013/0041690 A1 | 2/2013 | Brough | |
| 2013/0124226 A1 | 5/2013 | Gedala | |

OTHER PUBLICATIONS

WayBackMachine, www.coastlineelderly.org, Jun. 18, 2004—Index htm, Mission.htm, lnfo.htm, Services.htm, Shine.htm.

Gibson, James L. et al.; Organizations: Behavior Structure Processes; 9th Edition, Times Mirror Higher Education Group; Chapter 7; 1997; pp. 176-191.

Grossman, Claudia, et al.; Chapter 5—Healthcare Data as a Public Good; Privacy and Security Clinical Data as the Basic Staple of Health Learning; Creating and Protecting a Public Good; Workshop Summary; 2010; pp. 171-202; The National Academies Press; Washington, DC.

Ash et al., Using Diagnoses to Describe Populations and Predict Costs, Spring 2000, Health Care Financing Review, pp. 7-28 (Year: 2000).

\* cited by examiner

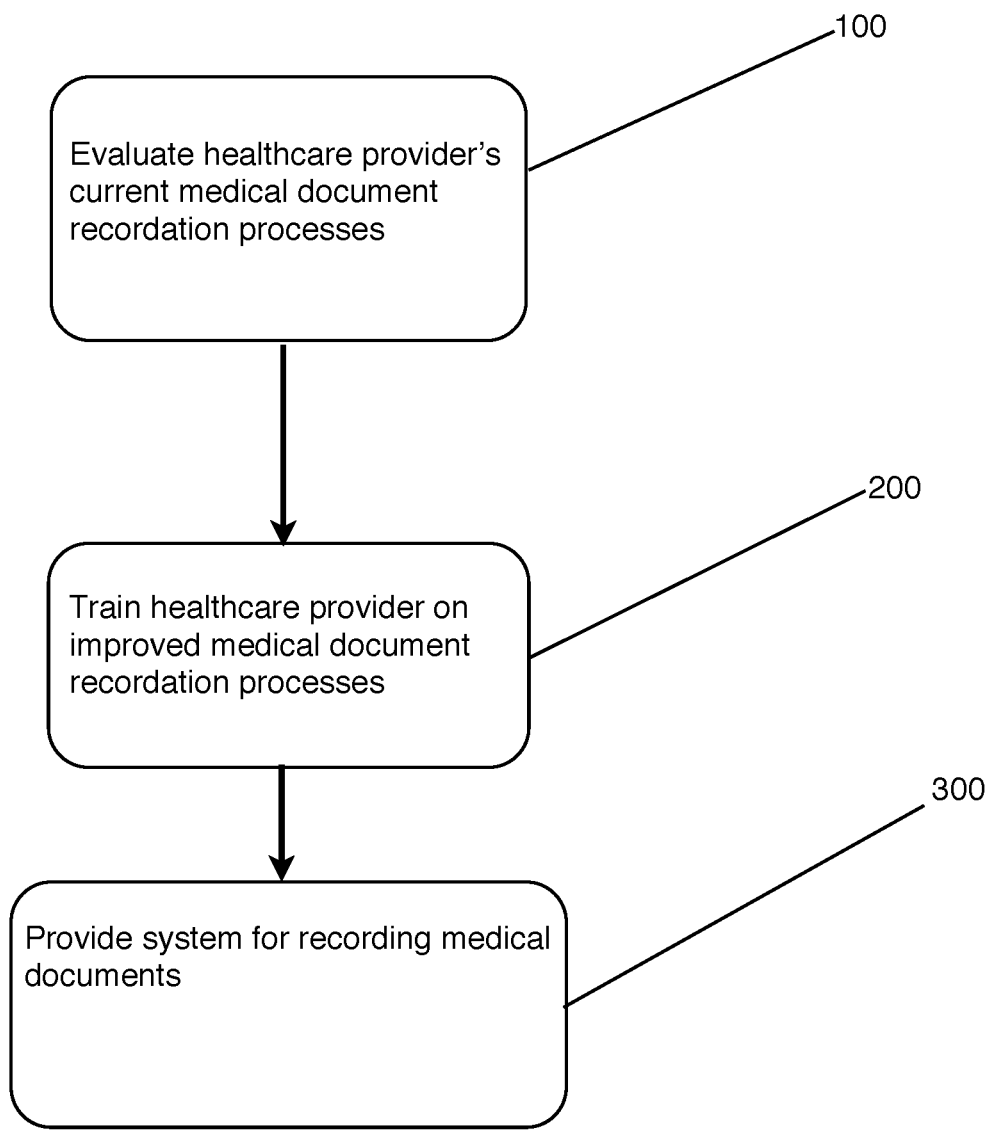

HIERARCHICAL CONDITION CATEGORIES PROGRAM

CROSS-REFERENCE TO RELATED APPLICATIONS

The present application is a continuation of U.S. patent application Ser. No. 15/691,413, filed Aug. 30, 2017 and entitled HIERARCHICAL CONDITION CATEGORIES PROGRAM, which is a continuation of U.S. patent application Ser. No. 14/326,754, filed Jul. 9, 2014 and entitled HIERARCHICAL CONDITION CATEGORIES PROGRAM, which is a continuation of U.S. patent application Ser. No. 13/167,976, filed Jun. 24, 2011 and entitled HIERARCHICAL CONDITION CATEGORIES PROGRAM, the entire contents of all of which are incorporated by reference herein.

STATEMENT RE: FEDERALLY SPONSORED RESEARCH/DEVELOPMENT

Not Applicable

BACKGROUND

The present invention is directed toward improved systems and methods for collecting and reporting Hierarchical Condition Categories (HCC). More particularly, the present invention comprises training programs and software systems useful by health plans and medical practitioners to more accurately code and report HCC to comply with the Centers for Medicare and Medicaid Services (CMS) documentation and reporting requirements.

Essential to high quality and cost-effective healthcare is the proper diagnosis of a patient's condition. From a proper diagnosis, the appropriate medical attention utilized to treat the underlying condition, whether it be the performance of a medical procedure, laboratory tests, and/or prescription of medication, can be determined. To that end, and as is well-known in the art, standard diagnoses codes are extensively utilized pursuant to conventional disease classification techniques that provide a quick, well-understood method to document medical care administered to a patient. Exemplary of, and perhaps most widely utilized of such formats, is the International Classification of Diseases 9th Edition (ICD-9) three digit codes. Likewise, with respect to the medical treatment that has been rendered, such procedures are typically referenced according to Current Procedural Terminology (CPT). Also frequently referenced in connection with the delivery of healthcare are drug codes (e.g., National Drug Code, or NDC), other service codes (e.g., Healthcare Common Procedure Coding System, or HCPCS), among others.

The Balanced Budget Act of 1997 (BBA) mandated a change in Medicare's payment methodology intended to pay health plans, and subsequently medical providers, based on a patient's health status through a process called Risk Adjustment Factor (RAF). Prior to the implementation of risk adjustment, reimbursement was based solely on demographic factors, such as, age, sex, Medicaid status, county of residence, etc.

In 2004, the Centers for Medicare and Medicaid Services (CMS) implemented a new model, the Hierarchical Condition Categories (HCC), as an additive model to adjust Medicare capitation payments to private healthcare plans for their expenditure risk of enrollees based on serious or chronic conditions. In theory, the CMS-HCC model pays more accurately for predicted health expenditures, based on health status and some demographic factors. In short, treat the patient appropriately and get reimbursed for doing so.

The collection and reporting of HCCs provides important benefits to patients and improves reimbursement. When health plans and/or practitioners have their own programs for documenting, auditing, and reporting HCCs, there is an opportunity to identify those at-risk enrollees/patients who, because of their disease markers, would benefit from increased frequency of visits and intensity of services, enrollment in complex care management, chronic care programs, and/or transitional care programs when appropriate—all designed to ensure the best possible clinical outcome for patients and cost savings for health plans and practitioners. Examples of such other programs are described in U.S. Pat. Nos. 7,657,442 and 7,464,041 and U.S. patent application Ser. Nos. 11/352,028 and 12/834,767, the entire teachings of which are collectively incorporated by reference herein.

Accordingly, there is a need in the art for a program designed to train and support health plans and practitioners the art and skill of correctly coding and reporting HCC to comply with CMS-HCC documentation and reporting requirements.

BRIEF SUMMARY

One aspect of the present invention is directed toward methods of recording a patient's medical documents. The methods include obtaining medical data from the patient, storing the data in electronic medical records embodied on a computer readable medium, evaluating the data via a computer capable of interpreting said electronic medical records to ensure that the data entry is complete, and presenting a notification to a user if any of the data is found to be incomplete or incorrect. The medical data obtained from the patient may include any of various relevant data, such as demographic information, medications taken, and symptoms suffered, but particularly includes disease codes. For example, the disease codes may be ICD-9 codes.

The data evaluation may take numerous forms, for example, whether for each disease code there is recorded a corresponding diagnosis of the disease, status of the disease, and plan of action for the disease and/or whether an improper code has been entered for each disease. More particularly, the obtained disease code may be evaluated to determine whether a more specific code should be used in its place. For example, whether a current disease has been improperly coded as a history of the disease. Another possible evaluation is whether there are likely disease codes that the patient may be suffering from that were not recorded. One example of this is when the patient is suffering from diabetes. A majority of patients suffering from diabetes have complications due to the diabetes. A notification may be provided to the user that complications of diabetes should be properly coded.

The medical data obtained may further include medication prescriptions of the patient and evaluating whether there is a linking disease code for each medication prescription. Additionally, a notification may be presented to the user of the system to review the medical records for commonly unreported diagnosed diseases within a set population of patients. Examples of commonly unreported diagnosed diseases include chronic kidney disease, neuropathy, peripheral vascular disease, and malnutrition.

Another aspect of the present invention is directed toward methods of training healthcare providers to properly record medical documents. This training includes evaluating the healthcare provider's current medical documentation process, training the healthcare provider in methods of recording medical documents, providing a system for recording medical documents, and training the healthcare provider in use of the system. The system includes a computer readable medium capable of storing medical data obtained from patients, including disease codes, a computer with software capable of evaluating the data stored on the computer readable medium for completeness, and a notification system capable of presenting to the user of the system a warning if any of the data is found to be incomplete or incorrect.

In particular, the training provided may include instructing the healthcare provider to ensure the medical documents are sufficiently detailed and coded to achieve the correct RAF score for each patient.

Yet another aspect of the present invention contemplates a system for recording medical documents. The system includes a computer readable medium capable of storing medical data obtained from patients, including disease codes, a computer with software capable of evaluating the data stored on the computer readable medium for completeness, and a notification system capable of presenting to the user of the system a warning if any of the data is found to be incomplete or incorrect.

For example, the notification system may present a warning if a disease code does not have a corresponding recorded diagnosis of disease, status of disease, and plan of action for the disease, if an improper disease code has been entered, if there are likely disease codes that have not been recorded and/or if a medical prescription is recorded without a linking disease code for the medication.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 1 is a flowchart depicting the steps for practicing the present invention as it relates to training healthcare providers in improved medical document recordation practices.

DETAILED DESCRIPTION

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

Referring now to FIG. 1, there is schematically illustrated the various steps by which a method of the present invention operates to train healthcare providers in improved medical document recordation practices. In particular, there is a first step 100 of evaluating the healthcare provider's current medical document recordation processes. For example, a team consisting of physicians, nurses, and financial auditors may conduct a two day on-site evaluation of the client's current HCC activities to determine data extraction and reporting methodology and validates the client's current RAF score.

A written report may be given to the client outlining the team's findings and recommendations that include staffing requirements, system requirements, and/or a program training and implementation work plan.

The second step 200 includes a comprehensive educational training program. For example, the training program may be offered as a ten day class with overhead presentations, case studies, and reference material, with topics including risk adjustment methodology, documentation training, Hierarchical Condition Coding (including commonly unreported or miscoded conditions), and training on systems for recording medical documents. The training section 200 may include a ninety day post-implementation followup with client's staff to evaluate program progress and/or an at least annual update to keep client apprised of changes in the CMS-HCC model.

The third step 300 is providing to the healthcare provider a system for recording medical documents, wherein the system includes at least a computer readable medium capable of storing medical data obtained from patients, wherein the data comprises disease codes; a computer with software capable of evaluating the data stored on the computer readable medium for completeness; and a notification system capable of presenting to the user of the system a warning if any of the data is found to be incomplete or incorrect. Examples of data to be recorded and warnings that may be presented by the system are discussed in greater detail below.

Risk Adjustment Methodology and Documentation Training

In order for the diagnostic classification system of the present invention to function properly the following principles may be used: 1) diagnostic categories should be clinically meaningful; 2) diagnostic categories should predict medical expenditures; 3) diagnostic categories that will affect payments should have adequate sample sizes to permit accurate and stable estimates of expenditures; 4) in creating an individual's clinical profile, hierarchies should be used to characterize the person's illness level with each disease process; 5) the diagnosis classification should encourage specific coding; 6) the diagnostic classification should not reward coding proliferation; 7) providers should not be penalized for recording additional diagnoses; 8) the classification system should be internally consistent; 9) the diagnostic classification should assign all ICD-9 codes; and 10) discretionary diagnostic categories should be excluded from payment models.

The Risk Adjustment Factor (RAF) is calculated by adding together a demographic factor (based upon, for example, the age and sex of the patient) and the total of a Hierarchical Condition Category (HCC) risk adjusted diagnosis. There are seventy disease categories, with over 3,100 diagnoses, available to apply toward the HCC risk adjusted diagnosis. A particular numerical "risk factor" is assigned to each category. Since the HCC is an additive model, the risk factor from all diagnoses are combined to reach the total RAF. Furthermore, the HCC is a predictive model, i.e., it is utilized to determine a future year payment based on coding this year's date of service. In summary, a higher RAF is obtained by sicker patients, thereby resulting in higher payments; whereas healthier patients will have a lower RAF, resulting in lower payments.

In particular, payments are determined through diagnosis coding after providing face to face patient evaluation at least once a year. As such, appropriate chart documentation and diagnosis reporting is required for accurate reimbursement. This documented information is submitted from the healthcare provider to the patient's health plan (HP), which in turn submits the data to the Centers for Medicare and Medicaid Services (CMS). CMS then takes the provided data and scrubs it for duplication and accuracy. The scrubbed data is then used by CMS to determine the revenue to provide to the HP. The HP then reimburses the health care provider based upon their contract. As such, it can readily be seen that proper diagnosis coding drives the RAF scorers, which in turn drives the reimbursement. Without proper documentation, the full reimbursement will not be retained.

It is important to note that with proper coding, patient care remains the priority. Once appropriate care is delivered to the patient, how to properly code for that care becomes important. However, care is not altered to meet coding strategies; rather, the reverse is the case, i.e., proper care drives proper coding. CPT codes reflect the level of care provided, but ICD-9 codes reflect the disease state addressed. Disease states submitted for a specific visit must be addressed and documented for that visit. The most missed diagnoses in senior patients are chronic kidney disease, peripheral vascular disease, peripheral neuropathy, and major depression. In order to properly document a patient visit, the chart must contain the patient's name (on each page, if the notes span multiple pages), the patient's date of birth or some other unique identifier, the date of service, and a handwritten or electronic signature of the caregiver, including credentials. Furthermore, validated HCC coding requires three documented points: 1) The diagnosis or assessment; 2) the status or condition (e.g., stable, condition worsening, medication adjusted, tests ordered, documentation reviewed, condition improving, etc.); and 3) a plan of action. Under the official ICD-9 coding guidelines, a diagnosis can only be coded when it is explicitly spelled out in the medical record. Accordingly, all documentation used for coding must be specific, and the mere fact that a patient has a condition is not sufficient on its own. Additionally, under ICD-9 guidelines, a diagnosis cannot be coded unless it is stated in the current visit documentation. All conditions that coexist at the time of the visit should be coded if they require or affect patient care, treatment, or management and are addressed in the medical record for the specified visit.

As discussed above, merely listing diagnoses is not sufficient documentation, as a diagnosis, status, and plan of action must all be documented for proper coding. Furthermore, merely listing medications does not meet documentation requirements to indicate that an evaluation for that condition was done. Also, superbills, encounter forms, and referrals are not acceptable forms of documentation as they are not considered a part of the medical record. Therefore, when a diagnostic report is provided it must be interpreted by the medical practitioner and documented for proper coding purposes. Additionally, a diagnosis must be presented unconditionally, without using terms such as "ruled out", "probable", "consistent with" and the like.

In an attempt to verify that diagnoses are being properly documented, CMS annually audits medical records. These audits are called Risk Adjustment Data Validation (RADV). Health plans, hospitals, medical groups, and physician offices are required to comply with CMS requests for medical records, and unsubstantiated diagnoses may result in recoupment of payments. In particular, the documentation substantiating that the patient was evaluated, monitored, or treated for the condition is a requirement for receiving reimbursement and must include all three of a diagnosis, status, and plan of action.

It is important to note that causal relationships of diseases need to be explicitly stated in the record, they cannot be inferred. Accordingly, linkage can be established in the chart with terms such as the specific disease being "due to", "associated with", "secondary to" or the like should be used to establish a cause and effect relationship. Terms such as "with", "probable", "more than likely" and the like do not sufficiently support linkage. For example, merely charting Type II Diabetes and Chronic Kidney Disease results in a significantly lower HCC RAF weight than would a proper charting of Type II Diabetes with Renal Manifestations and Chronic Kidney Disease due to Diabetes. Coding in the latter manner leaves no room for error in interpretation as to the disease states.

Another key aspect of proper charting is the correct documentation of a patient's "history of" a disease. The "history of" a disease should only be charted when the patient has been cured and is no longer being actively treated for the disease. A "history of" indicates that the medical condition no longer exists and the patient is not receiving any treatment, but there is the potential for recurrence and therefore requires continued monitoring. A "history of" a disease should not be used to describe a current acute or chronic condition even if it is controlled on medication. As long as the condition exists, despite totally successful and stable status, the condition must be coded as an active condition.

On an at least annual basis, a patient's chronic and active conditions should be documented so as to not overlook certain conditions. For example, chronic heart failure (CHF), chronic obstructive pulmonary disease (COPD), diabetes mellitus (DM), chronic kidney disease (CKD), neuropathy, and peripheral vascular disease (PVD) are chronic conditions that should be charted and are commonly unreported diagnoses. Furthermore, the patient's medication list should be reviewed to ensure there is a diagnosis associated with each medication. While patient care remains the priority at all times, without proper documentation in the medical record reimbursement will not occur. Following are certain examples of chronic conditions and proper methods of charting.

Diabetes

More than sixty percent of seniors with diabetes have a manifestation or complication of the diabetes. These complications must be properly charted, but are the most frequently omitted conditions in physician medical records. Good quality of care and reimbursement rely on the details. For example, it needs to be documented whether the patient suffers from Type I or Type II, whether there are complications associated with the diabetes, which systems are affected by the complications, and whether the blood glucose levels are controlled or uncontrolled.

When complications are due to diabetes, the documentation must make that connection explicitly. Additionally, every patient with diabetes should be evaluated for the many manifestations, complications, and co-morbidities of the disease, with progress notes and tests to show the evaluation was done. Exemplary possibilities are renal, ophthalmic, neurological, circulatory, other specified, and unspecified manifestations. Diabetes with manifestation codes have higher RAFs and, therefore, receive higher reimbursements. Even though only the highest weighted diabetes code will count toward the risk adjusted HCC model, all applicable manifestations should be charted.

Diabetes with manifestations require at least two separate codes; one for the diabetes with manifestation and one for the supporting associated diagnosis. For example, a patient with "diabetes with renal manifestation", aside from receiving a code for the diabetes, would also require a second code for what the manifestation is. Incomplete coding of the diabetes with renal manifestation by itself does not fully describe the manifestation or complication and would not receive the appropriate RAF.

Chronic Kidney Disease

Coding for CKD conforms to the stages of CKD, including stages I-IV based on a patient's glomerular filtration rate (GFR) (estimated from a urinalysis and/or serum creatinine levels) and/or kidney damage. However, some patients with "normal" creatinine levels have significant renal function impairment. As such, CKD-I and CKD-II are commonly missed. For those at risk of renal disease, creatinine clearance of GFR should be estimated at least twice per year. Further, the cause of the CKD should be checked and coded for a cause and effect linkage, for example, diabetes or hypertension. Unspecified kidney issue terminology such as chronic renal disease, chronic renal failure, and chronic renal insufficiency do not affect the RAF and should be avoided in favor of more specific diagnoses.

Cardiology

An important issue when documenting a significant cardiac diagnosis is to be specific. For example, less specific terms, such as, coronary artery disease or atherosclerotic heart disease, should be avoided if the patient has more specific diagnoses, such as, angina or history of myocardial infarction (MI). An acute MI is considered to be present for the first eight weeks after occurrence. If a patient is seen eight weeks after an acute MI and has not continued anginal symptoms, the coding should be changed to recent, old, or history of MI.

Cardiac angina is coded if currently being treated and may be continue to be coded even if asymptomatic due to pharmacological treatment. Other ongoing chronic cardiac conditions, such as, atrial fibrillation or arrhythmias should be documented and coded whether symptomatic or asymptomatic if continued pharmacological treatment or interventional cardiology is present. Of note, congestive heart failure is always a chronic condition after diagnosis, and echocardiograms should be used to evaluate and document diastolic heart failure.

Malnutrition

Malnutrition is often observed in senior patients due to conditions that limit nutrient ingestion and absorption, such as, cancer, pancreatitis, alcohol abuse, liver disease, obesity, CHF, COPD, end stage renal disease (ESRD), celiac disease, cystic fibrosis, depression, and dementia. However, malnutrition is often underreported and merely reported as being "underweight", "failing to thrive", or "loss of appetite" which do not affect the RAF. In these situations, occurrences of malnutrition should be identified.

Psychiatry

Episodic mood disorders are mental diseases that include mood disturbances such as major depression. The characteristics of these mood disturbances should be carefully documented and specific mental disorder terminology should be used in the final diagnosis, otherwise there will be no RAF adjustment. Furthermore, maladaptive patterns of substance use, leading to clinical impairment or distress should be coded as a dependence, rather than abuse.

Oncology

Malignancies are only coded until the patient has completed definitive treatment, such as surgery, chemotherapy, and/or radiation therapy aimed at eradicating the malignancy. Furthermore, breast and prostate cancer patients on adjuvant therapy are coded as having the active disease. However, once a patient has completed therapy, he or she can only be coded with a "personal history of cancer" diagnosis even if undergoing surveillance for reoccurrence of the malignancy.

It is extremely important to document when metastatic disease is present, as it has a separate coding section and CMS-HCC payment group. In this case, lack of specificity in the documentation can lead directly to a lower payment rate. Often, metastases are not clearly identified, thereby improperly leading to the coding of multiple primary malignancy sites.

Podiatry

Commonly under-diagnosed HCC conditions may be uniquely discovered by podiatrists, such as peripheral vascular disease, peripheral neuropathy, and skin ulcers. Again, if these conditions are due to a patient's diabetes, it is important to document by using two separate codes: one for the diabetes with circulatory or neurological manifestations and one for the supporting manifestation code.

Software for Electronic Medical Records

As can be seen from the examples provided above, there are numerous pitfalls that can be fallen into when documenting a patient's medical record, resulting in improperly coded, and under-reimbursed, diagnoses. Certain goals of the present invention are to train caregivers to properly document medical diagnoses and to provide a software platform for taking, storing, and aiding the caregiver in properly coding the medical records of patients.

Aside from, and in addition to, the training provided to caregivers in proper coding methodologies, as discussed in greater detail above, the present invention envisions a software platform (herein referred to as iCode) to improve compliance with CMS's correct coding initiative and HCC extraction and reporting. iCode allows for the enhanced care of Medicare Advantage enrollees, provides valuable information to the caregiver at the point of care, reduces duplicate and costly services by providing a comprehensive clinical history for each patient, and assists with capturing qualifying CMS-HCC codes.

In particular, iCode is capable of importing data from a caregiver's current medical records, billing files, health plan claim files, and the like. iCode then auto-populates each field from the data import to create new electronic medical records, analyzes the data, and creates reports of the analyzed data. Examples of such reports include, patient demographic information, health plan eligibility history, outstanding tests/procedures affecting performance per HEDIS measurements, summary of reported chronic conditions, list of potential unreported HCCs per review category, list of three year medical history by ICD-9 and CPT classifications, last six months of pharmacy data, and notes and comments. All captured data fields can be output as an iCode report.

Of particular relevance, however, is the ability of iCode to recommend potential missed coding opportunities based upon the medical conditions that have been entered in relation to historically incorrectly reported or underreported conditions. For example, iCode may recommend to the caregiver that in order for proper coding, a diagnosis of a disease, the status of the disease, and a plan of action must all be recorded.

Similarly, iCode may recommend to the caregiver that certain disease codes which do not affect the RAF have similar codes that do affect the RAF and may have been overlooked. For example, if a caregiver records a "history of" a disease, when in fact the patient is still suffering from the disease state, or if the records indicate less specific terminology for a disease state which may be more accurately described with a condition that does affect the RAF.

Another example of a suggestion iCode may make to the care giver is whether related complications of a disease have been improperly coded, or not coded at all. For example, patients suffering from diabetes typically have other disease states that are complications from the underlying diabetes. Unless these conditions are coded as deriving from the underlying diabetes, the RAF score is not properly assigned.

Additionally, iCode may recommend, upon annual reviews, that each medication prescribed to the patient needs a corresponding disease diagnosis coded, or recommend potential commonly miscoded or unreported diseases, such as chronic kidney disease, peripheral vascular disease, or malnutrition.

Along these lines, the recommendations provided by iCode are just that, recommendations. It is noted that the iCode software will never make changes or adjustments on its own to the entered medical records, but rather acts as a warning system to the caregiver for potentially overlooked diagnoses that should be coded on further inspection by the caregiver.

Additional modifications and improvements of the present invention may also be apparent to those of ordinary skill in the art. Thus, the particular combinations of parts and steps described and illustrated herein is intended to represent only certain embodiments of the present invention, and is not intended to serve as limitations of alternative devices and methods within the spirit and scope of the invention.

What is claimed is:

1. A non-transitory computer readable medium storing software executable by a computer to perform operations for automated review of medical data, the operations comprising:

obtaining a hierarchical condition category (HCC) dataset of over 3,100 diagnoses arranged in a plurality of categories, each of the categories corresponding to an assigned numerical risk factor;

obtaining a first set of rules that define a risk adjustment factor (RAF) as a function of one or more patient demographic factors and one or more numerical risk factors of the HCC dataset;

importing data from a caregiver's medical records, billing files, and health plan claim files;

generating one or more electronic medical records;

auto-populating fields of the one or more electronic medical records with the imported data, the fields of the one or more electronic medical records including one or more fields of demographic factors corresponding to a patient;

obtaining a data file of one or more diagnoses corresponding to the patient, the data file generated by the caregiver's entry of data into a software platform at the point of care;

calculating an RAF according to the first set of rules at least in part by processing the HCC dataset of over 3,100 diagnoses with reference to the obtained data file, the RAF being calculated based on the demographic factors corresponding to the patient from the one or more electronic medical records and the numerical risk factors of the HCC dataset corresponding to the one or more diagnoses from the data file;

determining, based on the first set of rules and the HCC dataset, which of the one or more diagnoses did not affect the calculation of the RAF;

for each of the one or more diagnoses which did not affect the calculation of the RAF, selecting an alternate diagnosis that affects the RAF from the HCC dataset, the selection of the alternate diagnosis based on a similarity between the diagnosis which did not affect the RAF and the alternate diagnosis and including i) a selection of a disease state corresponding to any "history of" a disease or other non-specific terminology recorded in the data file and ii) a selection of a causal relationship corresponding to any non-specific linking language between diagnoses recorded in the data file; and issuing a warning to the caregiver over the software platform in response to the selection of one or more alternate diagnoses, the warning including a recommendation to replace the one or more diagnoses which did not affect the calculation of the RAF with the selected alternate diagnoses.

2. A non-transitory computer readable medium storing software executable by a computer to perform operations for automated review of medical data, the operations comprising:

obtaining a hierarchical condition category (HCC) dataset of over 3,100 diagnoses arranged in a plurality of categories, each of the categories corresponding to an assigned numerical risk factor;

obtaining a first set of rules that define a risk adjustment factor (RAF) as a function of one or more patient demographic factors and one or more numerical risk factors of the HCC dataset;

importing data from a caregiver's medical records, billing files, and health plan claim files;

generating one or more electronic medical records;

auto-populating fields of the one or more electronic medical records with the imported data, the fields of the one or more electronic medical records including one or more fields of demographic factors corresponding to a patient;

obtaining a data file of one or more diagnoses corresponding to the patient, the data file generated by the caregiver's entry of data into a software platform at the point of care;

calculating a first RAF according to the first set of rules at least in part by processing the HCC dataset of over 3,100 diagnoses with reference to the obtained data file, the first RAF being calculated based on the demographic factors corresponding to the patient from the one or more electronic medical records and the numerical risk factors of the HCC dataset corresponding to the one or more diagnoses from the data file;

selecting, from the HCC dataset, one or more additional diagnoses by processing the HCC dataset with reference to the obtained data file, the selection of the one or more additional diagnoses based on a medical complication relationship between the one or more diagnoses from the data file and the one or more additional diagnoses and including a selection from the HCC dataset of a manifestation corresponding to any diabetes with manifestations recorded in the data file;

calculating a second RAF according to the first set of rules at least in part by processing the HCC dataset with reference to the obtained data file, the second RAF being calculated based on the demographic factors corresponding to the patient from the one or more electronic medical records, the numerical risk factors of the HCC dataset corresponding to the one or more diagnoses from the data file, and the numerical risk factors of the HCC dataset corresponding to the selected one or more additional diagnoses; and issuing a warning to the caregiver over the software platform in response to the selection of one or more additional diagnoses resulting in a second RAF greater than the first RAF, the warning including a recommendation to add the selected one or more additional diagnoses.

3. A system for automated review of medical data, the system comprising:

one or more computers;

one or more computer readable media storing i) a hierarchical condition category (HCC) dataset of over 3,100 diagnoses arranged in a plurality of categories, each of the categories corresponding to an assigned numerical risk factor, and ii) a first set of rules that define a risk adjustment factor (RAF) as a function of one or more patient demographic factors and one or more numerical risk factors of the HCC dataset; and a software platform that executes on the one or more computers to import data from a caregiver's medical records, billing files, and health plan claim files, generate one or more electronic medical records, and auto-populate fields of the one or more electronic medical records with the imported data, the fields of the one or more electronic medical records including one or more fields of demographic factors corresponding to a patient;

wherein the one or more computers are operable to obtain a data file of one or more diagnoses corresponding to the patient, the data file generated by the caregiver's entry of data into the software platform at the point of care, and calculate an RAF according to the first set of rules at least in part by processing the HCC dataset of over 3,100 diagnoses with reference to the obtained data file, the RAF being calculated based on the demographic factors corresponding to the patient from the one or more electronic medical records and the numerical risk factors of the HCC dataset corresponding to the one or more diagnoses from the data file;

wherein the one or more computers are further operable to determine, based on the first set of rules and the HCC dataset, which of the one or more diagnoses did not affect the calculation of the RAF and, for each of the one or more diagnoses which did not affect the calculation of the RAF, select an alternate diagnosis that affects the RAF from the HCC dataset, the selection of the alternate diagnosis based on a similarity between the diagnosis which did not affect the RAF and the alternate diagnosis and including i) a selection of a disease state corresponding to any "history of" a disease or other non-specific terminology recorded in the data file and ii) a selection of a causal relationship corresponding to any non-specific linking language between diagnoses recorded in the data file; and wherein the one or more computers are further operable to issue a warning to the caregiver over the software platform in response to the selection of one or more alternate diagnoses, the warning including a recommendation to replace the one or more diagnoses which did not affect the calculation of the RAF with the selected alternate diagnoses.

4. A system for automated review of medical data, the system comprising:

one or more computers;

one or more computer readable media storing i) a hierarchical condition category (HCC) dataset of over 3,100 diagnoses arranged in a plurality of categories, each of the categories corresponding to an assigned numerical risk factor, and ii) a first set of rules that define a risk adjustment factor (RAF) as a function of one or more patient demographic factors and one or more numerical risk factors of the HCC dataset; and a software platform that executes on the one or more computers to import data from a caregiver's medical records, billing files, and health plan claim files, generate one or more electronic medical records, and auto-populate fields of the one or more electronic medical records with the imported data, the fields of the one or more electronic medical records including one or more fields of demographic factors corresponding to a patient;

wherein the one or more computers are operable to obtain a data file of one or more diagnoses corresponding to the patient, the data file generated by the caregiver's entry of data into a software platform at the point of care, and calculate a first RAF according to the first set of rules at least in part by processing the HCC dataset of over 3,100 diagnoses with reference to the obtained data file, the first RAF being calculated based on the demographic factors corresponding to the patient from the one or more electronic medical records and the numerical risk factors of the HCC dataset corresponding to the one or more diagnoses from the data file;

wherein the one or more computers are further operable to select, from the HCC dataset, one or more additional diagnoses by processing the HCC dataset with reference to the obtained data file, the selection of the one or more additional diagnoses based on a medical complication relationship between the one or more diagnoses from the data file and the one or more additional diagnoses and including a selection from the HCC dataset of a manifestation corresponding to any diabetes with manifestations recorded in the data file;

wherein the one or more computers are further operable to calculate a second RAF according to the first set of rules at least in part by processing the HCC dataset with reference to the obtained data file, the second RAF being calculated based on the demographic factors corresponding to the patient from the one or more electronic medical records, the numerical risk factors of the HCC dataset corresponding to the one or more diagnoses from the data file, and the numerical risk factors of the HCC dataset corresponding to the selected one or more additional diagnoses; and wherein the one or more computers are further operable to issue a warning to the caregiver over the software platform in response to the selection of one or more additional diagnoses resulting in a second RAF greater than the first RAF, the warning including a recommendation to add the selected one or more additional diagnoses.

\* \* \* \* \*